US006170684B1

(12) United States Patent
Vincent et al.

(10) Patent No.: US 6,170,684 B1
(45) Date of Patent: Jan. 9, 2001

(54) FLASK VENT AND METHOD OF MAKING SAME

(76) Inventors: Monty E. Vincent, 3575 Miller Rd., Ann Arbor, MI (US) 48103; John R. Costello, Jr., 3169 Gove Dr., Tecumseh, MI (US) 49286

( * ) Notice: Under 35 U.S.C. 154(b), the term of this patent shall be extended for 0 days.

(21) Appl. No.: 08/606,596

(22) Filed: Feb. 26, 1996

(51) Int. Cl.[7] ................................................. B65D 53/00
(52) U.S. Cl. ..................... 215/261; 215/248; 215/364; 215/308; 215/DIG. 3
(58) Field of Search ................................... 215/248, 261, 215/308, DIG. 3, 355, 364; 220/371

(56) References Cited

U.S. PATENT DOCUMENTS

| | | |
|---|---|---|
| 2,153,981 | 4/1939 | Heineman . |
| 2,186,908 * | 1/1940 | Page et al. ............................ 215/248 |
| 2,191,447 * | 2/1940 | Beardsley ............................ 215/248 |
| 3,019,932 | 2/1962 | Singiser . |
| 3,313,712 | 4/1967 | George . |
| 3,326,401 | 6/1967 | De Long . |
| 3,952,902 | 4/1976 | Prouty et al. . |
| 4,136,796 | 1/1979 | Dubois et al. . |
| 4,235,344 | 11/1980 | Kulle et al. . |
| 4,271,973 * | 6/1981 | Quagliaro et al. .................... 215/308 |
| 4,935,371 * | 6/1990 | Rickloff ............................ 215/261 X |
| 5,037,754 | 8/1991 | Tanaka et al. . |
| 5,180,073 * | 1/1993 | Fay et al. ............................. 215/261 |
| 5,188,628 * | 2/1993 | Rani et al. ....................... 215/261 X |
| 5,358,872 | 10/1994 | Mussi et al. . |
| 5,395,006 | 3/1995 | Verma . |
| 5,522,769 | 6/1996 | Deguiseppi . |

FOREIGN PATENT DOCUMENTS

| | | |
|---|---|---|
| 265723 * | 12/1965 | (AU) ................................... 215/248 |
| 582 541 | 1/1993 | (CH) . |
| 2900807 * | 7/1979 | (DE) ................................... 215/248 |
| 0 007 261 | 1/1980 | (EP) . |
| WO 88 01605 | 3/1988 | (WO) . |

OTHER PUBLICATIONS

Brochure, "Steri Plug" (CTC Corp. Huntington, New York).
Brochure, "Closures, Silicone Sponge".

* cited by examiner

Primary Examiner—Stephen K. Cronin
(74) Attorney, Agent, or Firm—Kohn & Associates

(57) ABSTRACT

A closure (20) for sealing a micro-organism container (50) is disclosed. The closure (20) includes a resilient seal (24) for sealing the container (50), a passageway (26) extending through the seal (24), or filter media (28) extending across the passageway (26) integrally molded to the seal (24) for allowing sterile gas exchange therethrough. A method of making a flask closure (20) is also disclosed. The method includes molding a sealing member (24) having a passageway (26) extending therethrough while simultaneously sealing a peripheral edge (31) of a filter media (28) within the passageway (26).

6 Claims, 1 Drawing Sheet

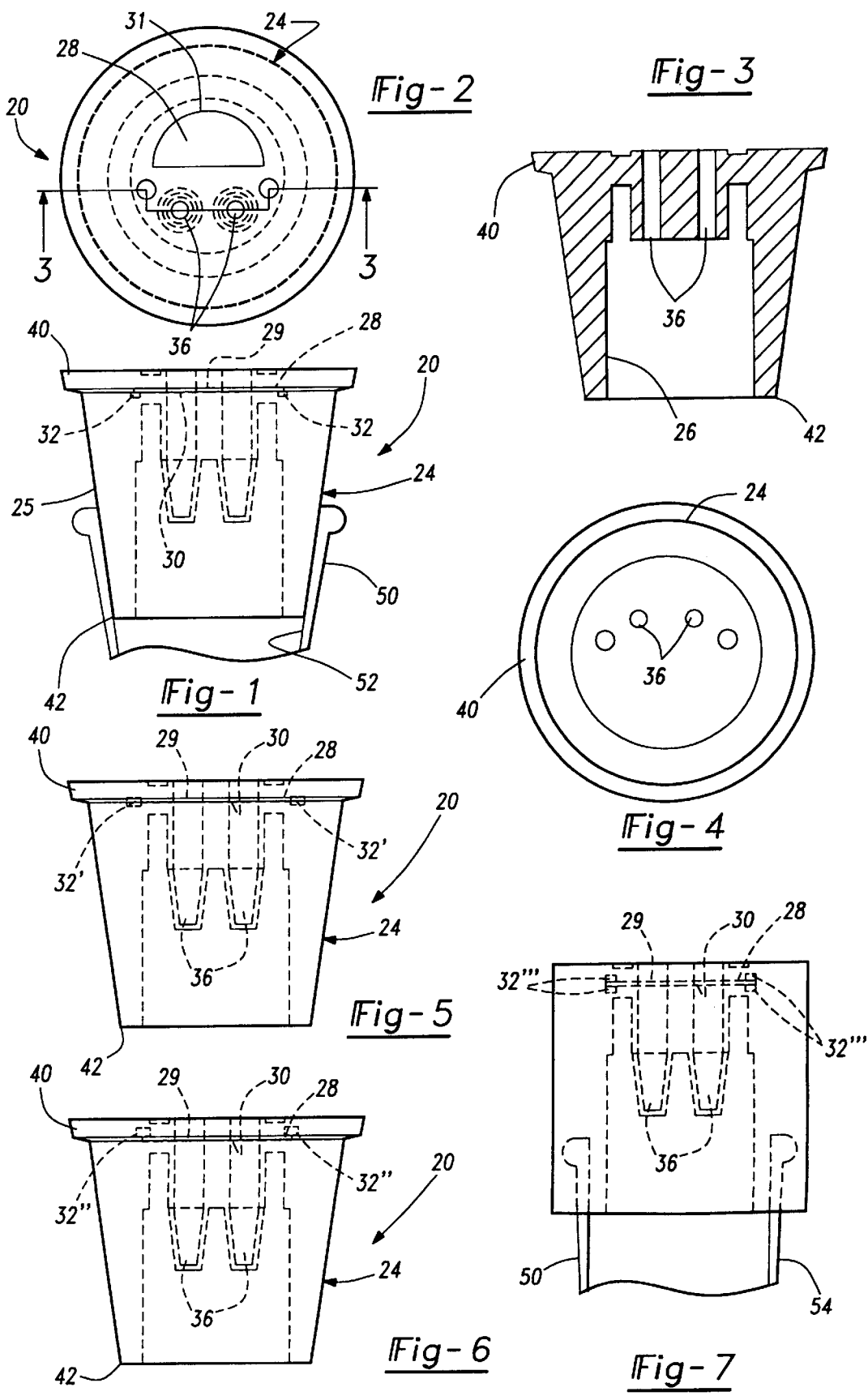

FLASK VENT AND METHOD OF MAKING SAME

TECHNICAL FIELD

The present invention relates to a closure. More specifically, the present invention relates to a closure for allowing sterile gas exchange therethrough.

BACKGROUND OF THE INVENTION

The use of closure devices for covering microbiological vessels, such as flasks, has been a widely accepted and longly used practice in microbiology. Closures are used in order to prevent the contamination of microorganisms being cultured or stored within the flasks by airborne contaminates or particulate matter. Additionally, these closures have been used to prevent the escape of microorganisms being cultured or stored in the flasks from being released from the flasks where they can become airborne and become contaminates themselves.

It is, generally, an absolute necessity that microorganisms or cultures must be grown under sterile conditions. Depending on the type of microorganism being cultured, either aerobic or anaerobic, closures have been designed to accommodate the specific growth requirements for each of these types of microorganisms. For example, aerobic microorganisms are only able to live in the presence of oxygen whereas anaerobic microorganisms are capable of growing, and in some circumstances are unable to grow, in the presence of oxygen. Therefore, for anaerobic organisms a closure may be required which is capable of maintaining sterile conditions within the interior of the flask or vessel by preventing the introduction of contaminating microorganisms while at the same time preventing the entrance of oxygen into the container or vessel.

Another requirement for a microbiological vessel or flask closure is that while maintaining the sterility of the microorganisms or cultures being grown therein, the closure should provide free access into the container or flask to facilitate the addition or removal of contents from the vessel or flask, such as sterile removal of microbiological culture from the vessel or flask.

Historically, cotton or gauze was formed into a plug and was inserted into the opening of a container or flask. These cotton or gauze plugs serve the general purpose of preventing contamination of the container or flask while simultaneously permitting the free exchange of oxygen with the atmosphere. This type of closure has many deficiencies such as it can be difficult to resterilize the plug for subsequent use and after repeated usage, this type of plug tends to readily decompose.

Another type of similar closure is described in U.S. Pat. No. 3,326,401 to De Long. This closure is adapted to fit over the open end of a microorganism container. The closure further includes a disposable plug made from a porous material which is positioned within the closure. This device has the deficiency that it does not allow for a seal between the closure and the container or flask to be established.

Another more recent development in microbiological container or flask closures provides the advantage of a filtering device combined with a plug type closure. This closure is referred to as the Steri Plug (CTP Corp. Huntington, N.Y.). This device is constructed of multiple components including a stopper portion, a filter, and associated gaskets and retainers. Because of its complex design, this type of closure is expensive and cumbersome to use.

Therefore, it would be desirable to have a closure assembly for use with microbiological containers or flasks in which the closure assembly includes a filter membrane and a seal which allows for creating an air and fluid tight seal between the closure and the container or flask and in which the closure assembly can be produced in a one step process thereby eliminating the complexity and lowering the cost of assembly and manufacture and eliminating the deficiencies described above for prior art closure devices.

SUMMARY OF THE INVENTION AND ADVANTAGES

In accordance with the present invention, there is provided a closure for sealing a microorganism container which includes a resilient seal for sealing the container, a passageway extending through the seal, and a filter media extending across the passageway integrally molded to the seal for allowing sterile gas exchange therethrough.

The present invention further provides a method of making a flask closure by molding a seal having a passageway extending therethrough while simultaneously sealing a peripheral edge of a filter media within the passageway.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 is a side view of a closure assembly in accordance with the present invention;

FIG. 2 is a top view of a closure assembly in accordance with the present invention;

FIG. 3 is a cross-sectional view of FIG. 2 taken along line 3—3;

FIG. 4 is a top view of a preferred embodiment of the present invention;

FIG. 5 is a side view of a preferred embodiment of the present invention;

FIG. 6 is a side view of a preferred embodiment of the present invention; and

FIG. 7 is a side view of another embodiment of the present invention.

DETAILED DESCRIPTION OF THE INVENTION

Referring to the Figures, a closure assembly for sealing a microorganism container is generally shown and designated by the reference numeral 20. Referring specifically to FIG. 1, the closure assembly 20 includes a resilient seal or plug 24 for sealing the closure 20 to a container 50. The closure assembly 20 further includes filter media 28 integrally disposed within the seal or plug 24 for allowing sterile gas exchange therethrough.

The container 50 can be a flask or other known type of container which retains liquids and microorganisms therein for the purpose of propagating aerobic or anaerobic microorganisms. The container 50 is preferably made of glass or pyrex® or other suitable materials which can withstand autoclaving or other such methods of sterilization.

The closure 20 can also include a port or passageway 26 axially disposed within the seal or plug 24 which extends through the seal or plug 24 allowing fluid communication between the container 50 and the external atmosphere. The passageway or port 26 is defined by a cylindrical side wall 25.

In one embodiment, the seal or plug 24 is generally frustoconical in cross-section. That is, the seal or plug 24 can be tapered and have a shape similar to a wedge. When an insertion end 42 of the seal or plug 24 is inserted into the container 50, the closure assembly 20 forms an air and liquid-tight seal with an inner surface 52 of the container 50. That is, the side wall 25 of the seal or plug 24 is graduated and, therefore, it can be inserted into containers 50 having variously sized openings therein and form an air and liquid-tight seal therewith. The cross-sectional diameter of the wall 25 of the seal or plug 24 increases in the direction opposite of the insertion end 42 of the seal or plug 24 as shown in FIGS. 1 and 4. Since an infinite number of diameters can be accommodated, the closure assembly 20 can be used with and create both air and liquid-tight seals with variously sized containers 50.

Referring to FIG. 7, another embodiment of the closure assembly 20 is shown. In this embodiment, the closure 20 has a generally cylindrical shape and is designed to fit over the container 50 and forms an air and liquid tight seal with an outer surface 54 of the container 50. The embodiment shown in FIG. 7 can be made in any desired size and thereby can be constructed to fit any size container 50.

The resilient seal or plug 24 is a generally unitary member formed of a resilient material which is capable of conforming and sealing to the contours of the openings of flasks or containers 50. That is, the resilient seal or plug 24 is constructed of a material which is capable of deflecting and/or yielding to sealingly conform to or to sealingly engage with the inner surface 52 of a container such that both an air-and liquid-tight seal is formed and maintained therewith. The seal or plug 24 can be constructed or manufactured from suitable flexible and resilient materials, for example, silicones, natural or synthetic rubber materials, polyolefins, polyamides, co-polymers, and fluoroplastics. This list is not meant to be exhaustive and can include other suitable materials known to those skilled in the art without departing from the spirit of the present invention.

The closure assembly 20 further includes a filter media 28 in the form of a filter having a top surface 29, a bottom surface 30, and a peripheral edge 31 which extends across the port or passageway 26. In a preferred embodiment, the filter 28 is somewhat flat or disk-shaped. The peripheral edge 31 of the filter 28 is sealed within the port or passageway 26 which axially extends through the seal or plug 24. The seal between the peripheral edge 31 and the seal or plug 24 must be both air- and liquid-tight in order to maintain the integrity and/or sterility of the closure 20 and contents of the container 50. The filter media 28 must be positioned and affixed within the port or passageway 26 such that any fluids (gaseous or liquid) can only pass through the filter media 28 and not around the periphery of the filter media 28 thereby breaching the sterility of the closure 20/container 50 system. In other words, the peripheral edge 31 of the filter media 28 must be affixed to the plug or seal 24 in such a manner to form a seal therein such that when the closure 20 is in place in the opening of the container 50, fluid and/or gas exchange can only occur across the filter media 28 thereby maintaining the sterility of the container 50 and its contents.

The filter 28 can be sealed within the passageway 26 of the seal or plug 24 by affixing or integrally molding the filter 28 within the port or passageway 26.

Referring to FIGS. 1, 5, 6, and 7, there is shown additional embodiments of the present invention. The embodiments illustrated in FIGS. 1, 5, 6, and 7 are similar in certain respects, accordingly, like elements have been designated with like prime numerals.

In order to provide rigidity in support to the filter 28, a support 32, 32', 32", 32''' can be provided adjacent to the filter 28.

Referring specifically to FIG. 1, the support can be disposed about and below the peripheral edge 31 of the filter 28. Referring specifically to FIG. 5, the support 32' can be disposed about the peripheral edge 31 at a position approximately level with the position of the peripheral edge 31. Referring specifically to FIG. 6, the support 32" can be disposed about and above the peripheral edge 31 of the filter 28. In all of the embodiments shown in FIGS. 1, 5, 6, and 7, the support 32, 32', 32", 32''' can be a ring molded or affixed to either the bottom of the peripheral edge 31, the top of the peripheral edge 31, or molded or affixed to the peripheral edge 31 in the same plane as the filter 28 or molded or affixed to both the top and bottom of the peripheral edge 31. The support can be constructed of any suitable materials including a metal, such as stainless steel, and plastic. The material comprising the support 32 must be able to withstand the temperatures and pressures encountered during autoclaving.

Alternatively, the support 32, 32', 32", 32''' can include a mesh-like matrix disposed on either the top 29, bottom 30, or both top 29 and bottom 30 of the filter 28 (not shown). The support member 32, 32D', 32", 32''' can be constructed of any suitable material, such as the same material as comprises the closure 20.

The filter 28 and the support 32, 32', 32", 32''' are positioned within the port or passageway 26 of the seal or plug 24 and can be fixed in place by means such as affixation during molding of the seal or plug 24 or can be positioned and fixed in place following molding of the seal or plug 24 such as by gluing or embedding the filter 28 and support 32, 32', 32", 32''' in the plug or seal 24 to the seal closure 20.

The filter 28 and the support 32, 32', 32", 32''' can be affixed to one another by means including molding or other types of affixation such as gluing or cementing.

The filter media 28 can include any suitable materials or membranes such as depth media including HEPA or ULPA rated glass microfiber, hydrophobic membranes such as polypropylenes, polytetrafluoroethylenes (PTFE), and polysulfones. This list of materials is not intended to be exhaustive and other suitable materials known to these skilled in the art can be utilized without departing from the spirit of the present invention. The filter media 28 is made from a material which is capable of permitting the exchange of gas thereacross, but will not permit the passage of micro-organic contaminants.

Referring specifically to FIG. 3, the closure assembly 20 can include at least one aperture or opening 36 extending therethrough to allow for the insertion of tubing, thermometer or the like therein. Since the aperture 36 is disposed within the seal or plug 24, the aperture 36 is able to conform and perfect a seal about any tubing or the like placed therein. The aperture 36 allows for sterile access to the interior of the container 50 and the contents therein without the risk of introducing any contamination.

The present invention further provides a method of making a flask closure 20 by molding the seal or plug 24 having the port or passageway 26 extending therethrough while simultaneously sealing the peripheral edge 31 of the filter media 28 within the port or passageway 26. That is, a one-piece, unitary closure assembly 20 is formed while simultaneously sealing the peripheral edge 31 of the filter 28 within the passageway 26 in the seal or plug 24. The molding step is accomplished by techniques well known to these skilled in the art.

The present invention can be practiced with various shape filter medias 28 as shown in FIG. 1 and FIG. 4 as long as the filter media 28 can be supported and the peripheral edge 31 of the filter media 28 is available for sealing affixation to the passageway 26 of the sealer plug 24.

The method of forming the closure assembly 20 can also include the step of disposing the support 32, 32', 32", 32''' within the passageway 26 either during the molding step or following the molding step. The method generally includes sizing the filter media 28 to a desired size. The supports 32, 32', 32", 32''' can also be specifically dimensioned. The filter media 28 and the supports 32, 32', 32", 32''' can be loaded into a mold cavity and are held in place on top of core pins by locator pins. A suitable material, such as silicone, can then be injected into the mold cavity. The silicone fills the mold cavity and encapsulates the filter media 28 and supports 32, 32', 32", 32''' and can then be cured by means such as utilizing heat from the mold. After a suitable curing period, the closure assembly 20 can be removed from the mold.

Throughout this application various publications are referenced by citation or number. Full citations for the publication are listed below. The disclosure of these publications in their entireties are hereby incorporated by reference into this application in order to more fully describe the state of the art to which this invention pertains.

The invention has been described in an illustrative manner, and it is to be understood the terminology used is intended to be in the nature of description rather than of limitation.

Obviously, many modifications and variations of the present invention are possible in light of the above teachings. Therefore, it is to be understood that within the scope of the appended claims, reference numerals are merely for convenience and are not to be in any way limiting, the invention may be practiced otherwise than as specifically described.

What is claimed is:

1. A closure (20) for sealing a micro-organism container (50), said closure (20) comprising:

a resilient plug member (24) for sealing the container (50);

a passageway (26) extending through said plug member (24) and filter media of material different from that of said plug member (24) extending across said passageway (26) and integrally molded to said plug member (24) for allowing sterile gas exchange therethrough, said plug member being a unitary member having a port (26) extending therethrough defining said passageway and said filter media (28) being integrally molded within said port (26).

2. A closure (20) as set forth in claim 1, wherein said filter media includes a filter membrane (28).

3. A closure (20) as set forth in claim 2, wherein said filter membrane (28) is constructed of a hydrophobic material.

4. A closure (20) as set forth in claim 2, wherein said filter membrane (28) includes at least one support means (32, 32', 32", 32''') disposed adjacent to said filter membrane (28) for supporting said filter membrane (28).

5. A closure (20) as set forth in claim 1, wherein said plug member (24) includes at least one aperature (36) extending therethrough to allow insertion of tubing therein.

6. A closure (20) as set forth in claim 1, wherein said plug member (24) has a frustoconical cross section.

* * * * *